(12) United States Patent
Inoue et al.

(10) Patent No.: US 8,841,125 B2
(45) Date of Patent: Sep. 23, 2014

(54) CANCER TISSUE-DERIVED CELL MASS AND A PROCESS FOR PREPARING SAME

(71) Applicants: Renaissance Energy Investment Co., Ltd., Hyogo (JP); Osaka Prefectural Hospital Organization, Osaka (JP)

(72) Inventors: Masahiro Inoue, Osaka (JP); Masayuki Ohue, Osaka (JP)

(73) Assignees: Renaissance Energy Investment Co., Ltd., Hyogo (JP); Osaka Prefectural Hospital Organization, Osaka (JP)

( * ) Notice: Subject to any disclaimer, the term of this patent is extended or adjusted under 35 U.S.C. 154(b) by 0 days.

(21) Appl. No.: 14/231,278

(22) Filed: Mar. 31, 2014

(65) Prior Publication Data

US 2014/0227781 A1 Aug. 14, 2014

Related U.S. Application Data

(62) Division of application No. 13/254,162, filed as application No. PCT/JP2010/053253 on Mar. 1, 2010, now abandoned.

(30) Foreign Application Priority Data

Mar. 2, 2009 (JP) ................................. 2009-048478
Sep. 30, 2009 (JP) ................................. 2009-228536

(51) Int. Cl.
*C12N 5/02* (2006.01)
*C12N 5/09* (2010.01)

(52) U.S. Cl.
CPC .................................... *C12N 5/0693* (2013.01)
USPC ............................ 435/381; 435/325; 435/378

(58) Field of Classification Search
None
See application file for complete search history.

(56) References Cited

U.S. PATENT DOCUMENTS

| 2012/0164732 A1 | 6/2012 | Inoue et al. |
| 2013/0012404 A1 | 1/2013 | Inoue |

FOREIGN PATENT DOCUMENTS

| JP | 2-501746 A | 6/1990 |
| JP | 2002-173500 A | 6/2002 |
| JP | 2006-507327 A | 3/2006 |
| JP | 2009-501004 A | 1/2009 |
| JP | 2011-193728 | 10/2011 |
| WO | WO-2006/129735 A1 | 12/2006 |

OTHER PUBLICATIONS

Bjerkvig, R. et al. (1990) "Multicellular Tumor Spheroids from Human Gliomas Maintained in Organ Culture," Journal of Neurosurgery, 72(3):463-475.

(Continued)

*Primary Examiner* — Blaine Lankford
*Assistant Examiner* — Thomas J Visone
(74) *Attorney, Agent, or Firm* — Foley & Lardner LLP; Antoinette F Konski

(57) ABSTRACT

Disclosed is a novel cell mass derived from a cancer tissue, which can reflect the in vivo behavior of a cancer cell correctly. Also disclosed is a process for preparing the cell mass. Specifically disclosed is a cell mass derived from a cancer tissue, which is an separated product that is isolated from a cancer tissue obtained from an individual as a mass containing at least three cancer cells or a cultured product of the separated product and which can retain a proliferation ability in vitro. The cell mass derived from a cancer tissue is produced by, for example, a preparation process comprising the steps of: treating a pulverized product of a cancer tissue removed from a living body with an enzyme; and selecting and collecting a mass containing at least three cancer cells among from an enzymatic treatment product.

10 Claims, 10 Drawing Sheets

(56) References Cited

OTHER PUBLICATIONS

Cammareri, P. et al. (2008) "Isolation and Culture of Colon Cancer Stem Cells," Methods in Cell Biology, 86, Chapter 14:311-324.
Communication pursuant to Article 94(3) EPC in European Patent Application No. 10748714.2, dated Oct. 1, 2013, 4 pages.
Folkins, C. et al. (2007) "Anticancer Therapies Combining Antiangiogenic and Tumor Cell Cytotoxic Effects Reduce the Tumor Stem-Like Cell Fraction in Glioma Xenograft Tumors," Cancer Res., 67(8):3560-3564.
U.S. Appl. No. 13/768,964, filed Feb. 15, 2013, Inoue.
Fujii, Y. et al. (2009), "Mukessei Fuyu Baiyo kei o Mochiita Koku Henpei Johi Gan Saibo no Sphere Keiseino to sono Gan Kansaibo to shiteno Saibo Bunshi Seibutsugakuteki Tokusei [Sphere-Forming Ability of Oral Squamous Cell Carcinoma Cells and Their Cytological/Molecular Biological Characteristics as Cancer Stem Cells Assessed in Serum-Free Floating Cultures]," Journal of the Japanese Stomatological Society, 58 (4): 239.
Fukuda, M. (1994) "Characterization and Comparison of Human Breast Cancer Cells Cultured within Collagen Gels," Department of Surgery, Kurume University School of Medicine, 57:760-768.
Hamilton, G. (1998) "Multicellular spheroids as an in vitro tumor model," Cancer Letters, 131:29-34.
Herrman, R. et al. (2008) "Screening for compounds that induce apoptosis of cancer cells grown as multicellular spheroids," Journal of Biomolecular Screening, 13(1):1-18.
Hirschhaeuser, F. et al. (2010) "Multicellular tumor spheroids: An underestimated tool is catching up again," Journal of Biotechnology, 148(1):3-15.
Hu, X. et al. (2005), "A study on the effect factors of the primary culture of laryngeal squamous cell carcinoma," Journal of Capital University of Medical Sciences, 26(3):242-245.
Inoue, M. (Mar. 3-13, 2005) "Tumor hibernation," The $2^{nd}$ Annual Meeting for the Japanese Association for Cancer and Hypoxia Research, Presentation.
Inoue, M. (Nov. 26-27, 2011) "Hypoxia-induced Dormant State of Cancer Cells." The $9^{th}$ Annual Meeting for the Japanese Association for Cancer and Hypoxia Research, Poster.
Inoue, M. (Jun. 27, 2012) "Dormancy of cancer cells in hypoxia," Naito Conference, Abstract.
Inoue, M. (Jan. 17-18, 2013) "Dormant state of cancer cells and oncogenic pathway," Cancer Metabolism, Abstract.
International Congress of Metastasis Research Society (Sep. 4, 2012) "Metabolism of cancer cells in hypoxia."
International Preliminary Report on Patentability for International Application No. PCT/JP2011/050866 dated Aug. 16, 2012 (11 pages).
International Preliminary Report on Patentability (Chapter II of the Patent Cooperation Treaty) for International Application No. PCT/JP2010/053253 dated Jul. 19, 2011 (9 pages).
Kaidi, S. et al. (2001) "Effect of Conventional Controlled-Rate Freezing and Vitrification on Morphology and Metabolism of Bovine Blastocysts Produced In Vitro," Biology of Reproduction, 65:1127-1134.
Kojima, S. et al. (1994) "Experimental Studies on the Mechanism of Invasion and Metasis of Oral Squamous Cell Carcinoma," J. Jpn. Stomatol. Soc., 43(3):355-362.
Kondo, J. et al. (2011) "Retaining cell-cell contact enables preparation and culture of spheroids composed of pure primary cancer cells from colorectal cancer," Proceedings of the National Academy of Sciences 108(15):6236-6240.
Kreso, A. et al. (2008) "Colon Cancer Stem Cells," Curr. Protoc. Stem Cell Biol., 7:3.1.1-3.1.12.
Kubota, S. et al. (1990) "Laminin peptide . . . ," Jikken Igaku 8(1):55-57.
Kunz-Schughart, L.A. et al. (2004) "The use of 1-19 3-D cultures for high-throughput screening: The multicellular spheroid model," Journal of Biomolecular Screening, 9(4):273-285.
Kyle, A.H. et al. (2012) "Targeting Quiescent Tumor Cells via Oxygen and IGF-I Supplementation," Cancer Res., 72(3):801-809.
Nagle, R.B. et al. (1994) Adhesion Molecules, Extracellular Matrix, and Proteases in Prostate Carcinoma, J Cell Biochem, (Suppl 19):232-237.
Nagrath, S. et al. (2007) "Isolation of rare circulating tumour cells in cancer patients by microchip technology," Nature, 450:1235-1239.
Nakachi et al. (2005), "Haisengan ni Okeru BRAF Idenshi no Juyosei ni Tsuite [Importance of BRAF Gene in Pulmonary Adenocarcinoma]", The Journal of the Japanese Respiratory Society 43, special extra issue: 156, POS153.
Nakagawa et al. (2008), "Baiyo Koku Henpei Johi Gan Saibo no Kekkan Shinsei Kassei ni Okeru Teisanso Kankyo no Eikyo [Influence of Hypoxia on Revascularizing Activity of Cultured Oral Squamous Cell Carcinoma Cells]", Journal of the Japanese Stomatological Society 57 (1): 93, 1-DM-1-3.
Nederman, T. et al. (1984) "Demonstration of an extracellular matrix in multicellular tumor spheroids," Cancer Research, 44(7):3090-3097.
Nie, Y. et al. (2009) "Scalable Culture and Cryopreservation of Human Embryonic Stem Cells on Microcarriers," Biotechnol. Prog., 25(1):20-31.
Nobuaki, H. et al. (1998) Chemosensitivity tests including genetic methods to anticancer agents. Urinary cancer. A chemosensitivity test for human solid tumors using collagen-gel-droplet embedded cultures, Cancer Therapy & Host, 10(4): 409-415.
Office Action in Chinese Patent Application No. 201080009962.3, mailed Jun. 21, 2013.
Office Action in Chinese Patent Application No. 201080009962.3, mailed Dec. 31, 2013.
Office Action in Japanese Patent Application No. 2009-228536, mailed Feb. 10, 2014.
Non-Final Office Action in U.S. Appl. No. 13/522,877, dated Feb. 11, 2014, 13 pages.
Paduch, R. et al. (2005) "Vitamin D, tamoxifen and [beta]-estradiol modulate breast cancer cell growth and interleukin-6 and metalloproteinase-2 production in three-dimensional co-cultures of tumor cell spheroids with endothelium," Cell Biology and Toxicology, 21(5-6):247-256.
Restriction Requirement in U.S. Appl. No. 13/522,877, dated Sep. 25, 2013, 7 pages.
Restriction Requirement in U.S. Appl. No. 13/768,964, dated Feb. 26, 2014, 16 pages.
Ricci-Vitiani, L. et al. (2007) "Identification and Expansion of Human Colon-Cancer-Initiating Cells," Nature Letters, 445:111-115.
Roche, Liberase Blendzymes Product Guide (2006).
Shmelkov, S.V. et al. (2008) "CD133 Expression is not Restricted to Stem Cells, and Both CD133+ and CD133- Metastatic Colon Cancer Cells Initiate Tumors," The Journal of Clinical Investigation, 118(6):2111-2120.
Supplementary European Search Report for European Patent Application No. 10748714.2, mailed Apr. 5, 2013, 9 pages.
Sutherland, R.M. (1988) "Cell and Environment Interactions in Tumor Microregions: The Multicell Spheroid Model," Science, 240(4849):177-184.
The $85^{th}$ Annual Meeting of Japanese Biochemical Society (Dec. 14, 2012) "Hypoxia induces tumor dormancy."
Takamura, Y. et al. (2002) "Prediction of Chemotherapeutic Response by Collagen Gel Droplet Embedded Culture-Drug Sensitivity Test in Human Breast Cancers," Int. J. Cancer, 98:450-455.
Takeda, T. et al. (2012) "Hypoxia inducible factor-1α is necessary for invasive phenotype in Vegf-deleted islet cell tumors," Scientific Reports, 2(494):1-7.
Todaro et al. (2007) "Colon Cancer Stem Cells Dictate Tumor Growth and Resist Cell Death by Production of Interleukin-4," Cell Stem Cell, 1:289-402.
Urazumi, K. (1989), "Human breast cancer cells under serum-free culture, its hormone dependency and application to the primary culture," Journal of Japan Surgical Society, 91(6):718-728.
Vermeulen, L. et al. (2008) "Single-Cell Cloning of Colon Cancer Stem Cells Reveals a Multi-Lineage Differentiation Capacity," PNAS, 105(36):13427-13432.

(56) References Cited

OTHER PUBLICATIONS

Wang et al. (2008), "Advance in evaluation and prediction model of available phosphorus in feed," Review Papers, 44(1): 54-57.

Written Opinion of the International Preliminary Examining Authority for International Application No. PCT/JP2010/053253 dated Apr. 5, 2011 (4 pages).

Xiao, Y. et al. (2008) "The Lymphovascular Embolus of Inflammatory Breast Cancer Expresses a Stem Cell-Like Phenotype," Am J Pathol., 173(2):561-574.

Zhang, S. et al. (2008) "Identification and Characterization of Ovarian Cancer-Initiating Cells from Primary Human Tumors," Cancer Res, 68(11):4311-4320.

Non-Final Office Action in U.S. Appl. No. 13/768,964 mailed Jul. 1, 2014, 20 pages.

Goustin, A.S. et al. (1986) "Growth Factors and Cancer," Cancer Research, 46:1015-1029.

Isohashi, F. et al. (2008) "Insulin-like growth factor stimulation increases radiosensitivity of a pancreatic cancer cell line through endoplasmic reticulum stress under hypoxic conditions," Cancer Sci., 99:2395-2401.

Harris, A.L. (2002) "Hypoxia—A Key Regulatory Factor in Tumour Growth," Nature Reviews Cancer, 2:30-47.

Communication pursuant to Article 94(3) EPC in European Application No. 10748714.2, dated May 6, 2014, 4 pages.

Office Action in Chinese Patent Application No. 201080009962.3, mailed Jul. 11, 2014, 4 pages.

Bar=100 μm

CANCER TISSUE-DERIVED CELL MASS AND A PROCESS FOR PREPARING SAME

CROSS-REFERENCE TO RELATED PATENT APPLICATIONS

This application is a divisional of U.S. application Ser. No. 13/254,162, filed Mar. 14, 2012, which is a national stage entry under 35 U.S.C. §371 of International Application No. PCT/JP2010/053253, filed Mar. 1, 2010, which claims priority to Japanese Application No. 2009-048478, filed Mar. 2, 2009, and Japanese Application No. 2009-228536, filed Sep. 30, 2009, the contents of which are incorporated herein by reference in their entireties.

TECHNICAL FIELD

The present invention relates to a cell mass derived from a cancer tissue (a cancer tissue-derived cell mass) and a process for preparing the same. More particularly, the present invention relates to a cancer tissue-derived cell mass, which is able to reconstruct a cancer in vitro, and retain a proliferation ability.

BACKGROUND

Background Art

In recent years, therapeutic results of early-stage cancers have been drastically improved as a result of various studies that have been repeated to overcome cancers. However, it is still difficult to treat advanced-stage cancers, and cancers have continued to occupy the first place of the Japanese cause of death. According to vital statistics of 2007 by the Ministry of Health, Labour and Welfare, 340,000 people or more died of cancers a year.

For cancer research so far, especially when examining its behavior in vitro, experiments using a cancer cell line that has been subcultured and established under optimized culture conditions are the mainstream. These cancer cell lines include human breast cancer cell lines (MDF7, NCI/ADR HS578T, MDA-MB-22231/ATCC, MDA-MB-4335, MDA-N, BT-549, T-47D), human cervical cancer cell lines (HeLa), human lung cancer cell lines (A549, EKVX, HOP-62, HOP-92, NCI-H23, NCI-H226, NCI-H322M, NCI-H460, NCI-H522), human colon cancer cell lines (Caco-2, COLO 205, HCC-2998, HCT-15, HCT-116, HT29, KM12, SW-620), and human prostate cancer cell lines (DU-145, PC-3, LNCaP), etc., which have been widely used for research.

For diagnosis or treatment of cancer patients, it is said that primary culture of cancer cells is promising, and its research has been advanced. For example, a CD-DST method (Collagen gel droplet embedded drug sensitivity test) using a primary culture cell has been developed. This in vitro test method is a drug sensitivity test by embedding a tissue or a cell isolated from a patient into a collagen gel droplet, and examining the sensitivity by the combination of a three-dimensional culture and an image colorimetric quantification (for example, Non-Patent Document 1). However, as to the primary culture cell, its culture method has not been established yet, and its handling is difficult.

As a result of studies on cancer cells, cancer cells constituting a cancer may consist of a plurality of subpopulations which are each a small population called "tumor initiating cells" or "tumor stem cells" able to self-replicate, and a series of reports that support the existence of such subpopulations which are able to become a source of the majority of cancer cells through differentiation have been published (for example, Non-Patent Documents 2 and 3). Such stem cells can be obtained, for example, by separating a tumor removed from a living body into single cells and sorting them. Some of them are said to have a proliferation ability even in vitro (Non-Patent Document 4). However, there is a negative report (Non-Patent Document 5) to the theory to explain the origin of cancer in terms of the stem cell in this way, and thus such a theory still remains a hypothesis.

There are still many unknown points about cancer even in the current state where cancer research has been widely performed.

PRIOR ART DOCUMENTS

Non-Patent Documents

Non-Patent Document 1: Takamura Y, et al., (2002) Prediction of chemotherapeutic response by collagen gel droplet embedded culture-drug sensitivity test in human breast cancers. Int. J. Cancer, 98, 450-455.

Non-Patent Document 2: Vermeulen L, et al., (2008) Single-cell cloning of colon cancer stem cells reveals a multi-lineage differentiation capacity. PNAS Vol. 105 No. 36 13427-13432.

Non-Patent Document 3: Ricci-Vitiani L, et al., (2007) Identification and expansion of human colon-cancer-initiating cells. Nature Vol. 445 111-115.

Non-Patent Document 4: Todaro M, et al., (2007) Colon cancer stem cells dictate tumor growth and resist cell death by production of interleukin-4. Cell Stem Cell 1:389-402.

Non-Patent Document 5: Shmelkov S V, et al., (2008) CD133 expression is not restricted to stem cells, and both CD133+ and CD133− metastatic colon cancer cells initiate tumors. The Journal of Clinical Investigation Vol. 118 2111-2120.

SUMMARY

Problems to be Solved by the Invention

One of the objectives of the present invention is to provide a novel cell mass derived from a cancer tissue, which is able to reconstruct in vitro the in vivo cancer cell behavior, including drug-sensitivity and radiosensitivity, and which is useful as a sample for analysis and treatment of cancer.

A further objective of the present invention is to provide a novel cell mass derived from a cancer tissue, which is useful as a sample for studies on analysis and treatment of cancer because it is available for simply and easily producing a cancer animal model, and is efficiently able to establish tumors in a small amount when transplanted into different species of animals.

Solutions to the Problems

The present inventors have attempted to perform a sensitivity test for therapy in cancer patients in consideration of the possibility that the cell line which had been used as study materials for the cancer research was different from the patient's cancer, and, as a result of intensive studies on a primary culture method for cancer cells as study materials to solve the above problems, they have found a novel cell mass derived from a cancer tissue, and a process for preparing the same, thereby to complete the present invention.

In other words, it is an object of the present invention to provide a novel cell mass derived from a cancer tissue, and a process for preparing the same, which can accurately reflect in vitro the in vivo behavior of the cancer cell in a living body of an individual.

The present invention relates to a cancer tissue-derived cell mass, which is a separated product that is separated from a cancer tissue obtained from an individual as a mass containing at least three cancer cells or a culture of the separated product, and which can retain a proliferation ability in vitro.

The cell mass derived from a cancer tissue may be obtained by a process comprising the step of treating a cancer tissue from the individual with a collagenase-containing enzyme.

The cell mass derived from a cancer tissue may be obtained by a process comprising the step of treating the cancer tissue with a mixed enzyme comprising particularly at least one protease selected from the group consisting of C. histolyticum neutral protease, thermolysin, and dispase, and at least one collagenase selected from the group consisting of collagenase I, collagenase II, and collagenase IV.

The mixed enzyme may be LIBERASE BLENDZYME 1® (a mixture of purified collagenase isoforms I and II and a neutral protease).

The present invention also relates to a cancer tissue-derived cell mass, which contains a population of at least three cancer cells and which takes an almost spherical or ellipsoidal form.

The present invention also relates to a cancer tissue-derived cell mass, which contains a population of at least three cancer cells, and a basement membrane-like material present in the circumference of the population of the cancer cells, and which takes an almost spherical or ellipsoidal form.

It is preferred that the cell mass derived from a cancer tissue does not contain substantially any cells other than cancer cells.

The basement membrane-like material may be laminin.

The diameter of the cell mass derived from a cancer tissue may be 40 μm to 250 μm.

The cancer cell may be derived from epithelial cancer cells.

The cancer cell may be derived from colon cancer, ovarian cancer, breast cancer, lung cancer, prostate cancer, kidney cancer, bladder cancer, pharyngeal cancer, or pancreatic cancer.

The present invention also relates to a process for preparing a cancer tissue-derived cell mass, which comprises the steps of:

treating, with an enzyme, a pulverized product of a cancer tissue removed from a living body; and selecting and collecting a mass containing at least three cancer cells from an enzymatically treated product.

The preparation process may further comprise the step of culturing the collected component for at least three hours.

The selection and collection may be a collection using a sieve.

The step of selecting and collecting the mass containing at least three cancer cells may be a step of collecting an oversized component using a sieve with a mesh size of 40 μm and collecting an undersized component using a sieve with a mesh size of 250 μm.

The enzyme may be a collagenase-containing enzyme. This enzyme may be a mixed enzyme comprising at least one protease selected from the group consisting of C. histolyticum neutral protease, thermolysin, and dispase, and at least one collagenase selected from the group consisting of collagenase I, collagenase II, and collagenase IV.

The mixed enzyme may be LIBERASE BLENDZYME 1®.

The present invention also relates to the cell mass derived from a cancer tissue, which is obtained by the preparation process mentioned above.

Advantages of the Invention

The cell mass derived from a cancer tissue according to the present invention shows the same in vitro behavior as in a living body, and the cell mass having such a behavior can be reconstructed, as well as can retain a proliferation ability over a certain period of time. Such a cancer tissue-derived cell mass can be used in the amplification by culturing a cancer cell and also can be used widely and conveniently in a drug-sensitivity test or a radiosensitivity test in vitro. It is possible to use the cell mass for simply and easily producing a tumorigenic animal because said cell mass is excellent in establishing a tumor in different species of animals.

DETAILED DESCRIPTION OF THE PREFERRED EMBODIMENTS

Figure 1:
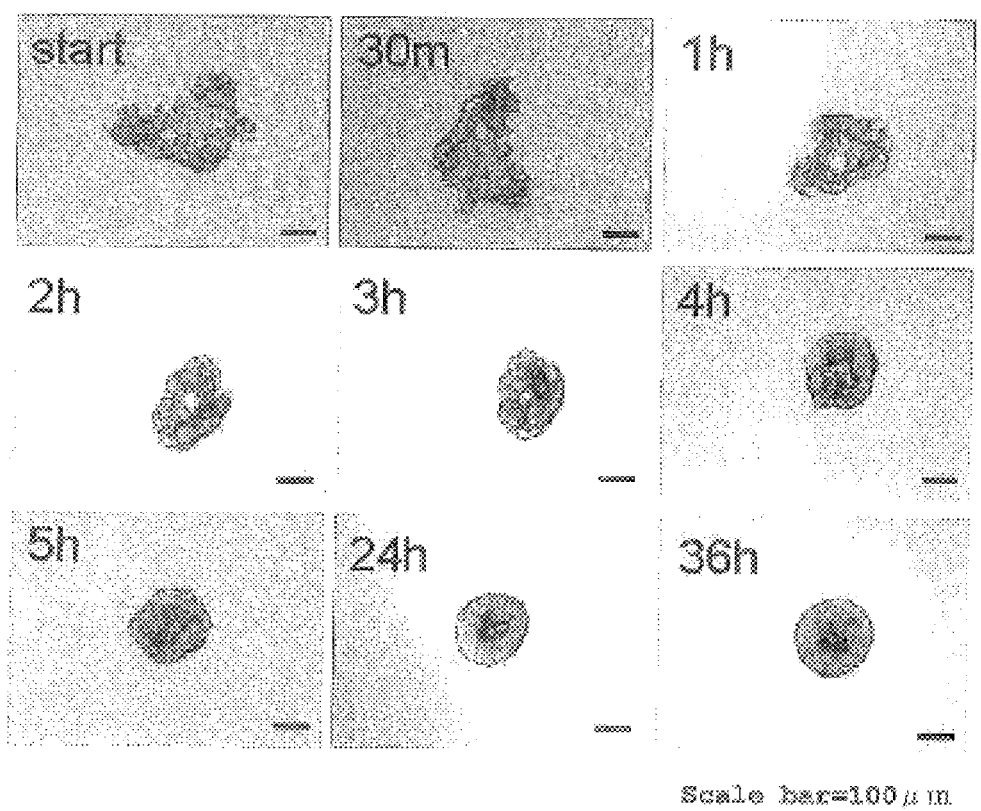
FIG. 1 is a drawing showing the formation process of the cell mass derived from a cancer tissue according to the present invention.

The cell mass derived from a cancer tissue according to the present invention is an separated product that is separated from a cancer tissue obtained from an individual as a mass containing at least three cancer cells or a cultured product of the separated product, and which can retain a proliferation ability in vitro.

Here, the expression of "a separated product that is separated from a cancer tissue obtained from an individual as a mass containing at least three cancer cells" means a separated product obtained by treatment of a cancer tissue of a cancer that has developed in a living body and contains at least three cancer cells, preferably at least eight cancer cells. Such a separated product does not include a product isolated to single cells as well as does not include a composition that has been once separated to single cells and has been then reconstructed. However, this separated product includes not only a product obtained just after separation from a living body, but also a product that is kept in, for example, a physiological saline solution for a certain period of time, or a product after freezing or cryopreservation.

The "cancer tissue obtained" from an individual refers to a cancer tissue obtained by surgical removal, etc., as well as a cancer tissue obtained with a needle or an endoscope so that it is possible to handle it in vitro for a tissue examination.

The expression of "a cultured product of a separated product that is separated from a cancer tissue obtained by separation from an individual as a mass containing at least three cancer cells" refers to a product obtained by culturing in vitro a separated product obtained by separation from a cancer tissue of a cancer that has developed in a living body as a mass containing at least three cancer cells. The culture time is not particularly limited, and the cultured product may include a cultured product that is allowed to be present in a medium even for a short time. This cultured product often takes an almost spherical or ellipsoidal form after being cultured for a certain period of time, preferably for at least three hours. The cultured product as described herein includes not only a cultured product with an almost spherical or ellipsoidal form after such a certain period of time, but also a cultured product with an irregular form before reaching such a spherical or ellipsoidal form. In addition, the cultured product as described herein includes a cultured product with an irregular form obtained by dividing such an almost spherical or ellipsoidal form, and a cultured product having an almost spherical or ellipsoidal form after further culture.

The expression of "can retain a proliferation ability" means that the cell mass derived from a cancer tissue according to the present invention can retain a proliferation ability in vitro for at least 10 days, preferably at least 13 days, and more preferably at least 30 days, under cell culture conditions of a temperature of 37° C. and a 5% $CO_2$-incubator.

Although such a cancer tissue-derived cell mass can retain a proliferation ability while continuing to culture without mechanical division for a period of at least 10 days, preferably at least 13 days, and more preferably at least 30 days, the proliferation ability can be retained substantially indefinitely by mechanically dividing the cell mass periodically during the culture.

The mechanical division of the cell mass can be performed using a surgical scalpel, knife, scissors, as well as an ophthalmic pointed knife. Alternatively, the mechanical division can also be performed by attaching an injection needle to a syringe and repeating suction and discharge of the cell mass derived from a cancer tissue together with a culture fluid. For example, a 1 ml syringe and a 27 G needle are preferably, but not limited to, used in the present invention.

Here, the medium for culture of the cell mass derived from a cancer tissue according to the present invention is not particularly limited, but an animal cell culture medium is preferably used. Especially preferably, a serum-free medium for stem cell culture is used. Such a serum-free medium is not limited at all so long as it can be used for stem cell culture. The serum-free medium refers to a medium which does not contain a non-adjusted and non-purified serum, and it can be used after addition of a purified blood-derived component or an animal tissue-derived component (e.g., a growth factor).

The serum-free medium of the present invention can be prepared using a medium used for animal cell culture as a basal medium. The basal medium includes, for example, BME medium, BGJb medium, CMRL 1066 medium, Glasgow MEM medium, Improved MEM Zinc Option medium, IMDM medium, Medium 199 medium, Eagle MEM medium, αMEM medium, DMEM medium, RPMI 1640 medium, Fischer's medium, and a combination thereof.

It is possible to culture the cell mass derived from a cancer tissue of the present invention by adding a serum substitute to such a serum-free medium. The serum substitute may be those appropriately containing, for example, albumin, an amino acid (e.g., non-essential amino acids), transferrin, a fatty acid, insulin, a collagen precursor, a trace element, 2-mercaptoethanol or 3'-thiolglycerol, or an equivalent thereof.

In the culture method of the present invention, a commercially available serum substitute can also be used. Examples of such a commercially available serum substitute include a knockout serum replacement (KSR), Chemically Defined Lipid Concentrate (manufactured by Gibco Company), and Glutamax (manufactured by Gibco Company).

The medium used for culturing the cell mass derived from a cancer tissue according to the present invention can also contain vitamins, growth factors, cytokines, antioxidants, pyruvic acid, buffers, inorganic salts, etc.

In particular, any serum-free media, such as a serum-free medium containing EGF and bFGF, for example, a serum-free medium containing a serum substitute [e.g. knockout serum replacement (KSR, manufactured by Invitrogen Corporation)] and bFGF can be preferably used. The content of the serum substitute or EGF is preferably 10 to 30% w/v based on the whole medium.

Such a medium is not limited, but a commercially available product includes a STEMPRO serum-free medium (Gibco) for human ES cells.

A culture vessel used for culturing the cell mass derived from a cancer tissue can include, but not particularly limited to, for example, flask, flask for tissue culture, dish, petri dish, dish for tissue culture, multi dish, micro plate, micro-well plate, multi plate, multi-well plate, chamber slide, schale, tube, tray, culture bag, and roller bottle, as long as the vessel is generally capable of culturing an animal cell therein.

The culture vessel can be cellular non-adhesive, and a three-dimensional culture is preferably performed in a medium in which a cell supporting substrate (e.g. an extracellular matrix (ECM), etc.) should be co-present. The cell supporting substrate can be any material intended to attach the cell mass derived from a cancer tissue. Examples of such a cell supporting substrate include Matrigel using an extracellular matrix, such as collagen gel, gelatin, poly-L-lysine, poly-D-lysine, laminin, fibronectin, etc. These conditions are preferably used particularly for the proliferation of the cell mass derived from a cancer tissue according to the present invention.

Other culture conditions can be appropriately set. For example, the culture temperature can be, but not limited to, about 30 to 40° C. and most preferably 37° C. The $CO_2$ concentration can be, for example, about 1 to 10% and preferably about 2 to 5%.

The cell mass derived from a cancer tissue according to the present invention can be cultured in such a medium under such a culture condition. Furthermore, for the culture of the cell mass derived from a cancer tissue, coculture with other cells may be desirable in some cases depending on individual properties, or a special additional supplement such as hormones may be necessary in some cases.

Specifically, coculture may be performed in the presence of feeder cells. For the feeder cells, stromal cell and the like such as fetal fibroblast may be used. Specifically, NIH3T3 and the like are preferable, but not limited to them.

Alternatively, in the case of a specific kind of breast cancer, uterine cancer, and prostate cancer, culture of such a cancer mass is performed preferably in the presence of a hormone. Specifically the hormone includes, but not limited to, estrogen for breast cancer, progesterone for uterine cancer, and testosterone for prostate cancer, and culture conditions can be conveniently adjusted while adding various hormones. In addition, hormone dependence of a cancer derived from a patient is understood by examining how behavior after culture of the cell mass derived from a cancer tissue is changed in the presence of such a hormone. As a result, effectiveness of an anti-hormone therapy may be predicted.

It is also possible to culture the cell mass derived from a cancer tissue according to the present invention by suspension culture. In the floating culture, the cell mass derived from a cancer tissue is cultured in a medium under a non-adhesive-condition to a culture vessel. Such a floating culture includes an embryoid culture method (see Keller et al., Curr. Opin. Cell Biol. 7, 862-869 (1995)), and an SFEB method (for example, Watanabe et al., Nature Neuroscience 8, 288-296 (2005); International Publication No. WO 2005/123902). The floating culture may be used in the production and maintenance of a stable cell mass derived from a tissue culture, which cell mass has, but not particularly limited to, an almost spherical form and has a basement membrane in some cases.

The cell mass derived from a cancer tissue according to the present invention includes a product just after separation from the cell mass derived from a cancer tissue of an individual, a product after freezing or cryopreservation, and further a cultured product thereof. The culture may be carried out for a period of time, such as preferably for at least three hours, more preferably for 10 to 36 hours, and still more preferably 24 to 36 hours or more.

The cancer cells constituting a cancer tissue-derived cell mass is composed of at least three cancer cells, preferably at least eight cancer cells, more preferably at least ten cancer cells, still more preferably at least 20 cancer cells, and most preferably at least 50 cancer cells. In the case where the cell mass derived from a cancer tissue according to the present invention is a separated product, it includes preferably 1000 cancer cells or less, and more preferably about 500 cancer cells or less. In the case of a cultured product after culturing the separated product, it is possible to increase the number of the cancer cells by culture. However, even the cultured product contains preferably 10,000 cancer cells or less, and more preferably 5000 cancer cells or less.

The term of "cancer cell" as used in the present invention is used in the sense commonly used, and refers to a cell where an order to be seen in normal cells is disordered, such as unrestricted division/proliferation and escape from apoptosis in a living body. More particularly, the term refers to a cell which has lost a control function for cell proliferation or refers to an extremely attenuated cell, and a cell which has typically acquired an infinite proliferation ability at high frequency of 80% or more, many of which also have an ability of invasion and metastasis, and, as a result, are regarded as a malignant neoplasm that causes the death particularly in a mammal including a human.

In the present invention, the kind of tissue derived from a cancer is not particularly limited, but it can be derived from cancers that are developed in an animal including a mammal, such as a lymphoma, a blastoma, a sarcoma, a liposarcoma, a neuroendocrine tumor, a mesothelioma, a neurinoma, a meningioma, an adenoma, a melanoma, a leukemia, and a malignant lymphoma, etc., and particularly preferably a carcinoma that is developed in mammalian epithelial cells. Examples of such a carcinoma that is developed in mammalian epithelial cells include a non-small cell lung cancer, a hepatocyte cancer, a bile duct cancer, an esophagus cancer, a stomach cancer, a colorectal cancer, a pancreatic cancer, a cervical cancer, an ovarian cancer, an endometrial cancer, a bladder cancer, a pharyngeal cancer, a breast cancer, a salivary gland cancer, a kidney cancer, a prostate cancer, a labia cancer, an anal cancer, a penis cancer, a testicular cancer, a thyroid cancer, and a head and neck cancer. The animal including a mammal includes, but not particularly limited to, an animal belonging to Primates such as monkey and human, an animal belonging to Rodentia such as mouse, squirrel, and rat, an animal belonging to Lagomorphahe, and an animal belonging to Carnivora such as dog and cat.

Among them, the cell mass of the present invention is particularly preferably derived from, but not limited to, a colon cancer tissue, an ovarian cancer tissue, a breast cancer tissue, a lung cancer tissue, a prostate cancer tissue, a kidney cancer tissue, a bladder cancer tissue, a pharyngeal cancer tissue, or especially a pancreatic cancer tissue.

In the case of a cancer tissue-derived cell mass derived from a colon cancer tissue, the cancer cell contained therein is not particularly limited, but may express CD133.

Separation of the cancer tissue obtained from a cancer that is developed in a living body is not limited, but includes an enzymatic treatment of a cancer tissue obtained from an individual.

The enzymatic treatment can be a treatment using one member of enzymes selected from collagenase, trypsin, papain, hyaluronidase, *C. histolyticum* neutral protease, thermolysin, and dispase, or a combination of two or more enzymes thereof. The conditions for such an enzymatic treatment may be as follows: in an isotonic salt solution (e.g. PBS or Hanks' balanced salt solution) buffered at a physiologically acceptable pH (e.g. about pH 6 to 8, preferably about pH 7.2 to 7.6) at for example about 20 to 40° C., preferably at about 25 to 39° C., for a time sufficient to degrade a connective tissue, for example, for about 1 to 180 minutes, preferably 30 to 150 minutes, with a sufficient concentration for such degradation, for example, about 0.0001 to 5% w/v, preferably about 0.001% to 0.5% w/v.

The conditions for such an enzymatic treatment include, but not limited to, a treatment with a mixed enzyme containing collagenase. For example, the enzymatic treatment includes a treatment with a mixed enzyme comprising one or more proteases selected from the group consisting of *C. histolyticum* neutral protease, thermolysin, and dispase, and one or more collagenases selected from the group consisting of collagenase I, collagenase II, and collagenase IV.

Such a mixed enzyme is not limited, but includes LIBERASE BLENDZYME 1® and the like.

The cell mass derived from a cancer tissue according to the present invention comprising optionally a population of at least three cancer cells may take an almost spherical or ellipsoidal form.

The cell mass may contain, but not limited to, a basement membrane-like material present in the circumference of said cancer cell population.

Here, the cancer cells constituting a population often have one or more surface antigens selected from the group consisting of, but not particularly limited to, CD133, CD44, CD166, CD117, CD24 and ESA on the cell surface. CD133, CD44, CD166, CD117, CD24 and ESA are surface antigens that are generally expressed in the cells such as leucocytes (e.g. lymphocytes), fibroblasts, epithelial cells, and cancer cells. These surface antigens are involved in various signal transmission in addition to a function of cell-cell adhesion and cell-matrix adhesion, and can also be surface markers for various stem cells.

When cell populations "express" surface antigens such as CD133 in the present invention, the term "express" means a state where 80% or more of the cells present in the cell populations, preferably 90% or more of the cells present in the cell populations, and more preferably substantially all of the cells present in the cell populations present surface antigens.

In the present specification, the term "basement membrane-like material" refers, but is not Limited, to a substance that contains preferably at least one member selected from collagen, laminin, nidogen and proteoglycans (e.g. heparan sulfate proteoglycan) and glycoproteins (e.g. fibronectin). In the present invention, a basement membrane-like material containing laminin is preferable.

Laminin is a high molecular weight glycoprotein that constitutes a basement membrane. The function of the laminin extends to a wide range, and is involved in, for example, cell functions such as cell adhesion, intercellular signal transmission, and proliferation of normal cells and cancer cells. The laminin has a structure wherein three different subunits are bonded to each other through a disulfide bond, and 11 kinds of laminins have been found depending on the different kinds of each subunit.

Of these, laminin-5 is usually produced only from an epithelial cell, and it is known as a component having activities to adhere to the basement membrane of the epithelial cell and promote a motor function. This laminin-5 has a composite structure that is formed from each one of α3 chain, β3 chain, and γ2 chain, and it is thought that particularly the γ2 chain is inherent to LN5 and is not contained in other LN molecular species.

The cancer tissue-derived cell mass according to the present invention may have a configuration such that the outer circumference of a population of cancer cells is, as a whole, wrapped in a film which is formed by such a basement membrane-like material. Such a form can be analyzed by observation of the cancer tissue-derived cell mass with an electron microscope, or by immunostaining of a basement membrane component, or by a combination thereof.

The presence of laminin can be detected, for example, by contacting an antibody that recognizes laminin (e.g. a rabbit antibody to a mouse laminin; Sigma-Aldrich Corporation) with a cancer tissue-derived cell mass, and measuring the antigen-antibody reaction.

Moreover, it is also possible to use a specific antibody that can specify even the type of the laminin. For example, the presence of laminin-5 can be detected, for example, by contacting an antibody that is reactive particularly to the above inherent γ2-chain or its fragment, with a cancer tissue-derived cell mass, and measuring the reaction with the antibody.

In the cancer tissue-derived cell mass according to the present invention, it is desirable that a thin filmy basement membrane-like material is formed in a size of about several micrometers, or about 40 to 120 nm, according to the size of masses, but the size is not limited to them.

The size of the cancer tissue-derived cell mass according to the present invention also includes, but not limited to, an irregular form with a particle size or a volume average particle size of about 8 μm to 10 μm, as well as further includes a particle size of 1 mm or more of the cell mass that has been grown up greatly after incubation. The diameter of the cell mass is preferably 40 μm to 1000 μm, more preferably 40 μm to 250 μm, and further more preferably 80 μm to 200 μm.

The cancer tissue-derived cell mass according to the present invention often has one or more arrangements particularly selected from the group consisting of, but not particularly limited to, palisade arrangement, sheet arrangement, multilayer arrangement, and syncytial arrangement.

The cancer tissue-derived cell mass according to the present invention may be prepared typically by a process which comprises the steps of treating a pulverized product of a cancer tissue removed from a living body, with an enzyme; and selecting and collecting a mass containing at least three cancer cells among from an enzymatic treatment product.

Moreover, the cancer tissue-derived cell mass according to the present invention may be prepared by, but not limited to, a process comprising the step of culturing the thus collected component for three or more hours.

At first the cancer tissue removed from a living body can be pulverized as it is, or the cancer tissue is first maintained in a medium for animal cell culture before pulverization. The medium for animal cell culture includes, but not particularly limited to, Dulbecco's MEM (DMEM F12, etc.), Eagle's MEM, RPMI, Ham's F12, alpha MEM, and Iscove's modified Dulbecco's medium. In this case, floating culture is preferably carried out in a culture vessel which is non-cell-adhesive.

It is also preferable to wash the cancer tissue in advance for pulverization. Such a washing can be carried out using, but not limited to, a buffer solution such as acetic acid buffer solution (acetic acid+sodium acetate), phosphoric acid buffer solution (phosphoric acid+sodium phosphate), citric acid buffer solution (citric acid+sodium citrate), boric acid buffer solution, tartaric acid buffer solution, Tris buffer solution, or phosphate-buffered saline. In the present invention, washing of the tissue can be performed particularly preferably in HBSS. As for the number of times of the washing, once to three times are suitable.

The pulverization can be performed by dividing the tissue after washing, with use of a knife, scissors, or a cutter (manual operation and automatic operation). The size and form after pulverization are not particularly limited, but the pulverization may be performed at random. The tissue is preferably pulverized to a uniform size, 1 mm to 5 mm square, more preferably 1 mm to 2 mm square.

The pulverized product thus obtained is then subjected to an enzymatic treatment. Such an enzymatic treatment can be a treatment using one member of enzymes selected from collagenase, trypsin, papain, hyaluronidase, *C. histolyticum* neutral protease, thermolysin, and dispase, or a combination of two or more enzymes thereof. The conditions for such an enzymatic treatment may be as follows: in an isotonic salt solution (e.g. PBS or Hank's balanced salt solution) buffered at a physiologically acceptable pH (e.g. about pH 6 to 8, preferably about pH 7.2 to 7.6) at for example about 20 to 40° C., preferably at about 25 to 39° C., for a time sufficient to degrade a connective tissue, for example, about 1 to 180 minutes, preferably about 30 to 150 minutes, with a sufficient concentration for such degradation, for example, about 0.0001 to 5% w/v, preferably about 0.001% to 0.5% w/v.

The conditions for this enzymatic treatment include, but not limited to, a treatment using a mixed enzyme containing, for example, collagenase. More preferably, the enzymatic treatment includes a treatment with a mixed enzyme comprising at least one protease selected from the group consisting of *C. histolyticum* neutral protease, thermolysin, and dispase, and at least one collagenase selected from the group consisting of collagenase I, collagenase II, and collagenase IV.

Such a mixed enzyme includes, but not limited to, LIBERASE BLENDZYME 1® and the like.

Among the enzymatic treatment products obtained in this way, it is preferable to select and collect a mass containing at least three cancer cells. The process for such selection and collection is not particularly limited, but any process well-known to those skilled in the art for assorting the size can be used.

Of the methods for assorting the size, a simple and easy process is a visual observation, a classification with a phase contrast microscope, or a classification with a sieve, but the classification method is not particularly limited so long as it is a classification with a particle size available for those skilled in the art. When a sieve is used, it is preferable to collect a component which passes through a sieve with a mesh size of 500 µm and does not pass through a sieve with a mesh size of 20 µm. It is more preferable to collect a component which passes through a sieve with a mesh size of 40 µm and does not pass through a sieve with a mesh size of 250 µm.

Here, the mass containing at least three cancer cells, which is a subject for selection, is a cancer tissue-derived cell mass according to the present invention and has a certain range of sizes. The term of "a certain range of sizes" includes small ones with a volume average particle size of about 8 µm to 10 µm. When the cell mass is in an almost sphere form, it has a diameter of 20 to 500 µm, preferably 30 to 400 µm, and more preferably 40 to 250 µm. When the cell mass is in an ellipsoidal form, it has a long diameter of 20 to 500 µm, preferably 30 to 400 µm, and more preferably 40 to 250 µm. When the cell mass is in an irregular form, it has a volume average particle size of 20 to 500 µm, preferably 30 to 400 µm, and more preferably 40 to 250 µm. The measurement of the volume average particle size can be performed by evaluating a particle size distribution and a particle shape using a CCD camera attached to a phase contrast microscope (IX70; manufactured by Olympus Corporation).

Both of the separated product and its cultured product, which are components obtained in this way by selection and collection, are a cancer tissue-derived cell mass according to the present invention. The cultured product may be those wherein the separated product as a component after selection and collection has been present in a medium for a short time, or those which are in an almost sphere or ellipsoidal form after culture for a period of time, for example, at least three hours, preferably 10 to 36 hours, and more preferably 24 to 36 hours or more. The culture time may be over 36 hours, several days, at least 10 days, at least 13 days, or at least 30 days.

The culture may be performed in a medium for a long time without any mechanical division, but a proliferation ability can also be retained for a substantially infinite time period by a mechanical division periodically during of culture.

The cancer tissue-derived cell mass according to the present invention shows an in vitro behavior similar to a cancer tissue in a living body and can be stably cultured while retaining its proliferation ability. Therefore, the cell mass is useful, for example, in identification of the type of the existing drugs to which the tumor that is derived from a cancer tissue obtained is susceptible, or in confirmation of the presence or absence of a radiosensitivity in each patient individually. The drug sensitivity or radiosensitivity can be determined by, but not limited to, any known methods. The drug sensitivity can be determined by measuring a proliferation rate of the cancer tissue-derived cell mass in vitro. Such measurements include, for example, a visual observation of viable cell count a few hours or a few days after addition of a test drug compared to a control example; an image analysis after taking a photograph with a CCD camera; or a colorimetry of an amount of a protein contained in each cell after staining it with a protein-binding dye (for example, sulforhodamine B).

Such a cancer tissue-derived cell mass is also useful for screening unknown drugs. This unknown drug sensitivity may also be determined by the measurement of a proliferation rate in vitro of a cell mass of a cancer tissue, or by the judgment of life and death of cells. The measurement of the proliferation rate includes, for example, a visual observation of viable cell count a few hours or a few days after addition of a test drug compared to a control example; an image analysis after taking a photograph with a CCD camera; a colorimetry of an amount of a protein contained in each cell after staining it with a protein-binding dye (sulforhodamine B); and a measurement of SD (succinyl dehydrogenase) activity.

The sensitivity measurement data of human cultured cells to test compounds, i.e. a concentration ($GI_{50}$) to inhibit the cell proliferation by 50%, a concentration (TGI) to suppress an apparent cell proliferation, and a concentration ($LC_{50}$) to decrease the number of cells to 50% at the time of seeding, are calculated to enable to perform an information processing. As for $GI_{50}$, TGI, and $LC_{50}$ values, a numerical value inherent to each of cell masses derived from cancer tissues to be tested is obtained. The overall average $GI_{50}$, TGI, and $LC_{50}$ values are obtained, the difference between this average value and Log $GI_{50}$ value in individual cells is determined, and, based on an average Log $GI_{50}$ value, such difference is made into an absolute value for expressing it in a positive or negative number. It can be judged that the sensitivity of a drug becomes higher as the positive number is increased.

As a radiosensitivity test using the cancer tissue-derived cell mass according to the present invention, it includes a known test using X-rays or γ-rays from a radioactive isotope of cobalt as a radiation source; particle rays obtained by accelerating an electron beam with a linear accelerator; or heavy corpuscular rays such as α-rays taken out by a cyclotron, singly or in combination of a radiosensitizer.

In addition, the cell masses derived from a cancer tissue according to the present invention, for example, even 10 or less cell masses (corresponding to 1,000 cells or less) having a diameter of 100 µm derived from a cancer tissue, have a high settlement rate in the transplantation in different species of animals. Therefore, the cancer tissue-derived cell mass according to the present invention is useful for a simple and easy production of a cancer model animal including a mouse, and makes it possible to examine a cancer tissue exactly, evaluate drug sensitivity, or evaluate a therapeutic embodiment including a radioimmunotherapy.

The cancer tissue-derived cell mass according to the present invention can be cryopreserved, and its proliferation ability can be retained under normal preservation conditions.

INDUSTRIAL APPLICABILITY

The cancer tissue-derived cell mass according to the present invention can be cryopreserved in vitro in a state where culture is possible, and can be used for a wide range of applications. In addition, the cell mass can be proliferated by culture, enabling to proliferate a cancer cell from a very small amount of specimen. Moreover, the cancer tissue-derived cell mass according to the present invention can be widely used for a drug sensitivity test or a radiosensitivity test, and can be used for a simple and easy production of a tumorigenesis animal. Therefore, the cancer tissue-derived cell mass according to the present invention can bring about a rapid improvement in anti-cancer drugs or radiotherapies which are currently used generally as a trial and error method or a cocktail therapy. In other words, before performing such a therapy, effects of drugs and radiotherapies can be predicted in advance with the cancer tissue-derived cell mass from each patient according to the present invention, and thus it is possible to administer only an effective drug to a patient. Moreover, since the cancer tissue-derived cell mass according to the present invention can be present in such a size that can be collected with an injection needle, it is also possible to obtain the cell mass from a patient before a surgical operation, as well as to predict an effect of an anti-cancer drug or a radiotherapy with low burdens on patients.

EXAMPLES

Hereinafter, the present invention will be specifically described by way of examples, but it is not limited to these examples. In addition, parts and percentages in each example are all based on a weight basis. The culture conditions below are, unless otherwise indicated, under incubator conditions of 37° C. and 5% $CO_2$. The centrifugal conditions are, unless otherwise specifically stated, 4° C., 1000 rpm, and 5 minutes.

Example 1

Preparation of Cell Mass Derived from Cancer Tissue of Colon Cancer Xenograft in Mice The colon cancer xenografts in mice were prepared by a xenograft procedure as shown below.

At first, a surgically resected specimen of a human tumor (colon cancer) is cut into small pieces (each about 2 mm cube) under aseptic conditions. Then, a small incision of about 5 mm was made at the back of mice (nude mice, preferably NOD/SCID mice) with a severe immunodeficiency, and a subcutaneous tissue is peeled from the animal. A tumor graft which has been prepared is subcutaneously inserted, and wound closure is performed with a skin suture clip. Some of the xenografts are observed as a subcutaneous tumor about 14 days later to three months later.

The produced mice bearing a colon cancer were bred under SPF (specific pathogen free) conditions, and when the tumor reached 1 cm in size, it is removed and collected into a 50 ml-centrifuge tube (IWAKI; 2345-050) containing 20 ml of DMEM (Gibco; 11965-092)+1% Pen Strep (Gibco; 15140-022) (both as a final concentration of 100 units/ml penicillin, 100 μg/mL).

Next, after addition of 20 ml of HBSS (Gibco; 14025-092), tumor was washed by inverting the tube for mixing. Then, 20 ml of a fresh HBSS was added, and these procedures were repeated twice, after which time the tumor tissue was transferred to a 10 cm-cell culture dish (Cell Culture Dish) (IWAKI; 3020-100). The necrotic tissue was removed with a surgical knife on this culture dish.

The tumor xenograft from which the necrotic tissue had been removed was transferred to a fresh 10 cm-dish in which 30 ml of HBSS had been added. Then, the tumor graft was pulverized into small pieces (each about 2 mm cube) using a surgical knife.

The pulverized tumor xenograft was transferred to a 50-ml fresh centrifugal tube, centrifuged, the supernatant was discarded, and the residue was washed by inverting the tube for mixing with a 20 ml HBSS.

The centrifugation and washing were repeated. After that, 20 ml DMEM+1% Pen Strep+0.28 U/ml (final concentration) BLENDZYME 1 (Roche; 11988417001) were added and mixed. This mixture was transferred to a 100 ml-Erlenmeyer flask and treated with LIBERASE BLENDZYME 1 (manufactured by Roche Diagnostics K.K.) in a thermostat bath of 37° C. while rotating it with a stirrer at a low speed for 2 hours.

Then, the enzymatic treatment product was collected into a 50 ml centrifuge tube, centrifuged, and the supernatant was discarded, after which time 20 ml of HBSS was added and mixed. The mixture was passed through a stainless steel mesh (500 μm), and the components that passed through the filter were collected into a 50 ml centrifuge tube, and further centrifuged. After discarding the supernatant, 1 mg/m DNase I solution (Roche; 1284932)(10 mg/ml stock 100 μl+PBS 900 μl) was added to the residue for mixing, and the mixture was allowed to stand at 4° C. for 5 minutes. After that, 20 ml-HBSS was further added, mixed, centrifuged, and the supernatant was discarded. The residue was mixed with 20 ml HBSS, sieved stepwise in the order of 500→250→100 μm, and then passed through a cell strainer of 40 μM (BD; 352340). The cell strainer was soaked in a 10 cm-tissue culture dish (Tissue Culture Dish) containing 30 ml of HBSS, and shaken slightly to remove single cells, small cell masses of 40 μm or less, and debris. The cell strainer was transferred to another 10 cm-tissue culture dish (Tissue Culture Dish) containing 30 ml of HBSS, and the cell mass that had been trapped in the cell strainer was collected by pipetting.

In addition, the same centrifugal separation as above was repeated several times, and 4 ml StemPro hESC SFM (Gibco; A10007-01)+8 ng/ml bFGF (Invitrogen; 13256-029)+0.1 mM 2-mercaptoethanol (Wako; 137-06862)+1% PenStrep+25 μg/ml Amphotericin B (Wako; 541-01961) were added to the resulting components, and mixed. The mixture was transferred to a 6 cm-non-treated dish (EIKEN CHEMICAL Co., Ltd.; AG2000).

This was cultured in an incubator (MCO-17AIC; manufactured by SANYO Electric Co., Ltd.) at 37° C. and 5% $CO_2$ for 36 hours.

As a result, the cell mass derived from the cancer tissue changed its irregular form into a regular sphere with the lapse of time as shown in FIG. 1, i.e., it became almost a sphere at least 3 to 6 hours later, and a completely regular sphere-shaped cell mass derived from the cancer tissue was obtained after 24 hours.

Example 2

Figure 7:
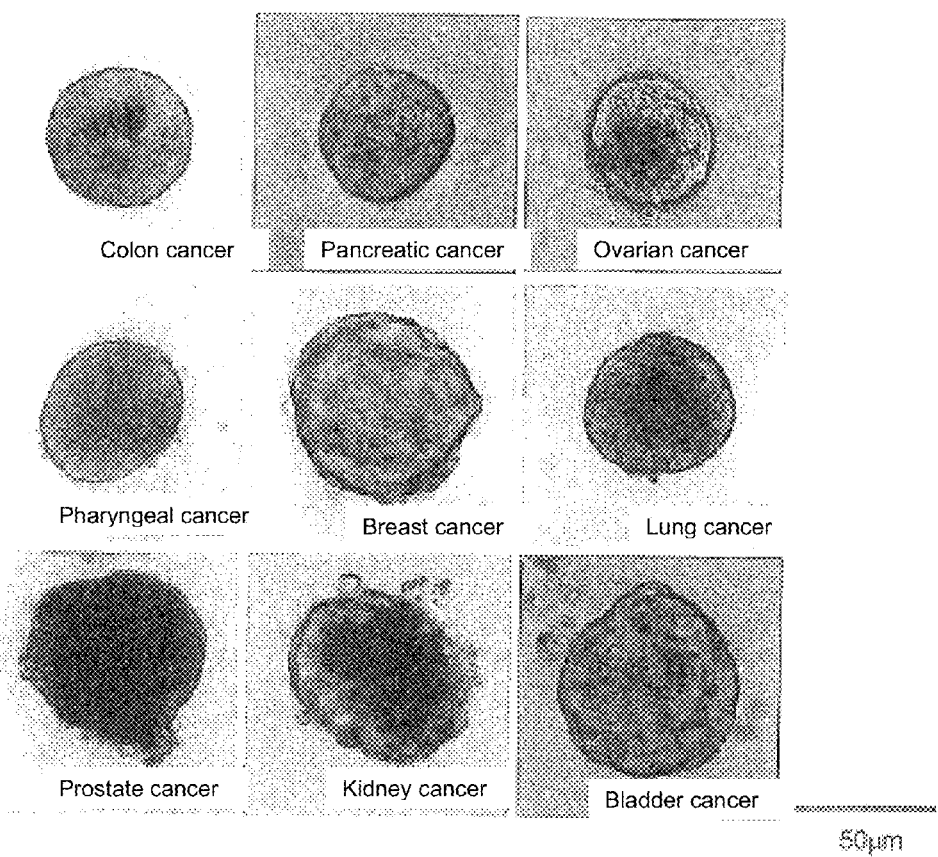
FIG. 7 is a drawing showing the cell mass derived from a cancer tissue according to the present invention, wherein the cell mass is obtained from various cancer tissues, and wherein colon cancer, pancreatic cancer, and ovarian cancer (upper part); pharyngeal cancer, breast cancer, and lung cancer (middle part); and prostate cancer, kidney cancer, and bladder cancer (lower part) are shown from the left.

Preparation of cell mass derived from cancer tissue from surgical specimens of human colon cancer The cell mass derived from the cancer tissue was obtained in the same manner as in Example 1, except that surgical specimens of colon cancer were used. As a result, an almost sphere-shaped cell mass derived from the cancer tissue, similar to one as shown in FIG. 1, was obtained at least 12 hours later as shown in FIG. 7.

Example 3

Preparation of Cell Mass Derived from Cancer Tissue from Surgical Specimens of Human Ovarian Cancer The cell mass derived from the cancer tissue was obtained in the same manner as in Example 2, except that surgical specimens of ovarian cancer were used. As a result, an almost sphere-shaped cell mass derived from the cancer tissue, similar to one as shown in FIG. 1, was obtained at least 12 hours later as shown in FIG. 7.

Example 4

Preparation of Cell Mass Derived from Cancer Tissue from Surgical Specimens of Human Pancreatic Cancer The cell mass derived from the cancer tissue was obtained in the same manner as in Example 2, except that surgical specimens of pancreatic cancer were used. As a result, an almost sphere-shaped cell mass derived from the cancer tissue, similar to one as shown in FIG. 1, was obtained at least 12 hours later as shown in FIG. 7.

Example 5

Preparation of Cell Mass Derived from Cancer Tissue from Surgical Specimens of Human Small Cell Lung Cancer The cell mass derived from the cancer tissue was obtained in the same manner as in Example 2, except that surgical specimens of human small cell lung cancer which is a kind of lung cancer, were used. As a result, an almost sphere-shaped cell mass derived from the cancer tissue, similar to one as shown in FIG. 1, was obtained at least 12 hours later as shown in FIG. 7.

Example 6

Preparation of Cell Mass Derived from Cancer Tissue from Surgical Specimens of Human Kidney Cancer The cell mass derived from the cancer tissue was obtained in the same manner as in Example 2, except that surgical specimens of kidney cancer were used. As a result, an almost sphere-shaped cell mass derived from the cancer tissue, similar to one as shown in FIG. 1, was obtained at least 12 hours later as shown in FIG. 7.

Example 7

Preparation of Cell Mass Derived from Cancer Tissue from Surgical Specimens of Human Bladder Cancer The cell mass derived from the cancer tissue was obtained in the same manner as in Example 2, except that surgical specimens of bladder cancer were used. As a result, an almost sphere-shaped cell mass derived from the cancer tissue, similar to one as shown in FIG. 1, was obtained at least 12 hours later as shown in FIG. 7.

Example 8

Preparation of Cell Mass Derived from Cancer Tissue from Surgical Specimens of Human Breast Cancer The cell mass derived from the cancer tissue was obtained in the same manner as in Example 2, except that surgical specimens of breast cancer were used. As a result, an almost sphere-shaped cell mass derived from the cancer tissue, similar to one as shown in FIG. 1, was obtained at least 12 hours later as shown in FIG. 7.

Example 9

Preparation of Cell Mass Derived from Cancer Tissue from Surgical Specimens of Human Prostate Cancer The cell mass derived from the cancer tissue was obtained in the same manner as in Example 2, except that surgical specimens of prostate cancer were used. Dihydrotestosterone (DHT) with a concentration of $10^{-8}$ mol/L was added to a medium, and culture was performed in the same manner as in Example 1. As a result, an almost sphere-shaped cell mass derived from the cancer tissue, similar to one as shown in FIG. 1, was obtained at least 12 hours later as shown in FIG. 7.

Example 10

Preparation of Cell Mass Derived from Cancer Tissue from Surgical Specimens of Human Pharyngeal Cancer The cell mass derived from the cancer tissue was obtained in the same manner as in Example 2, except that surgical specimens of pharyngeal cancer were used. As a result, an almost sphere-shaped cell mass derived from the cancer tissue, similar to one as shown in FIG. 1, was obtained at least 12 hours later as shown in FIG. 7.

Example 11

Hormone Sensitivity Test of Cell Mass Derived from Breast Cancer Tissue

Figure 8:
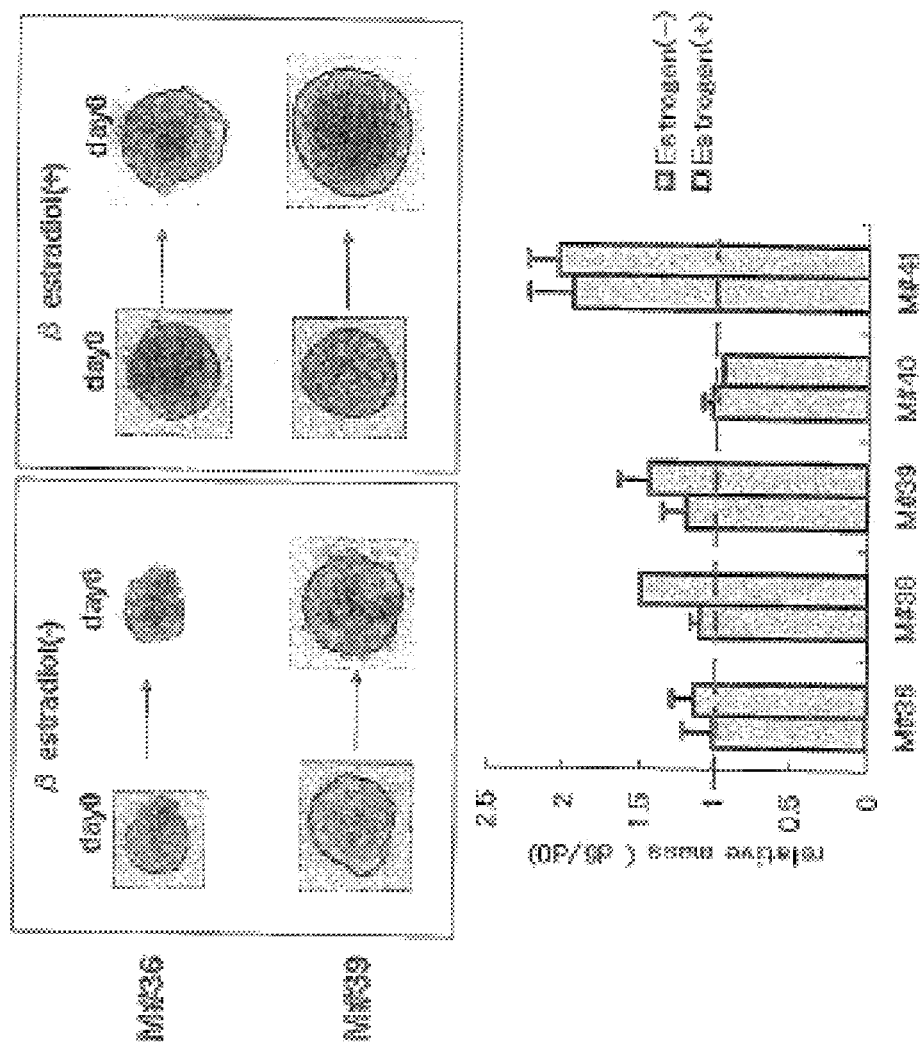
FIG. 8 is a drawing showing the result of a culture test for hormone sensitivity using the cell mass derived from a breast cancer tissue.

An investigation was made on how the state of each of the cell masses derived from the cancer tissues from a plurality of patients with breast cancers was different from each other by the presence or absence of estradiol under the same medium conditions as in Example 8. As a result, as shown in FIG. 8, it has been understood that there are a case where proliferation is promoted by the addition of estradiol and a case that does not respond to estradiol. This was found to be applicable as a sensitivity test in a hormone therapy of a patient from which the cell mass was derived.

Example 12

Figure 9:
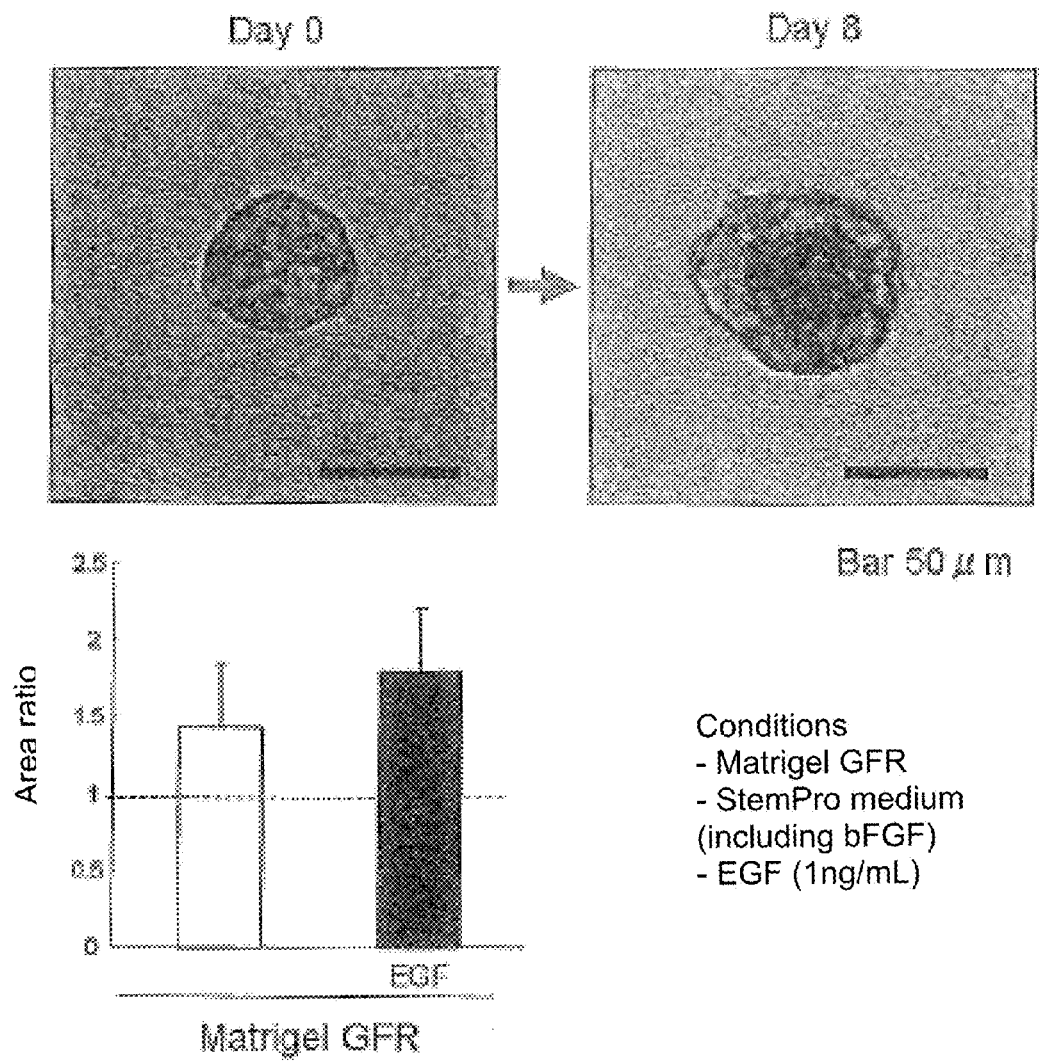
FIG. 9 is a drawing showing the cell mass derived from a cancer tissue according to the present invention, wherein the cell mass is obtained from a mouse pancreatic islet cell tumor.

Preparation of Cell Mass Derived from Cancer Tissue from Mouse Pancreatic Islet Cell Tumor RipTag is a transgenic mouse wherein SV40-T antigen is forcedly expressed under the control of a rat insulin promoter and a tumor occurs in the pancreatic islet. The cell mass derived from the cancer tissue was obtained in the same manner as in Example 2, except that the pancreatic islet tumor in RipTag mice was used. As a result, an almost sphere-shaped cell mass derived from the cancer tissue, similar to one as shown in FIG. 1, was obtained at least 12 hours later (FIG. 9).

Example 13

The cell mass derived from the cancer tissue under culture as shown in FIG. 7 obtained in Example 2 was taken out together with 5 ml of the medium 24 hours after culture, centrifuged at 1000 rpm and 4° C., and the supernatant was discarded. The collected cell mass derived from the cancer tissue was suspended in Cell Banker (BLC-1, manufactured by Mitsubishi Chemical Medicine Corporation) and 10 μM of Y27632 (manufactured by Wako Pure Chemical Industries, Ltd.) was further added thereto. The mixture was transferred to a cryopreservation tube (Cryogenic vials 2.0 ml, manufactured by Nalge Nunc Corporation) and preserved in a deep freezer at −80° C.

Figure 10:
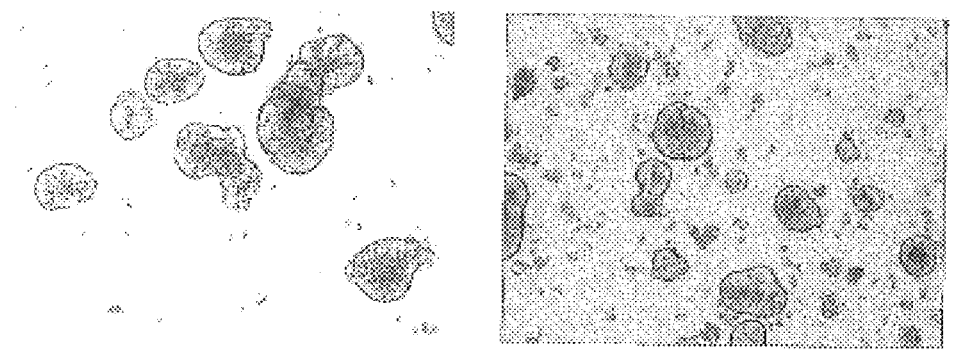
FIG. 10 is a drawing showing the result of comparing the states between before and after cryopreservation of the cell mass derived from a cancer tissue according to the present invention (left: before cryopreservation; right: 24 hours after thawing).

After 7-days preservation, the mixture was rewarmed in a water-bath of 37° C. for a short time. This was suspended in PBS, centrifuged at 1000 rpm and 4° C., and the supernatant was discarded. The resultant precipitate was suspended in StemPro (manufactured by Invitrogen) and cultured. As shown in FIG. 10, the cell state at 24 hours after thawing was excellent.

Furthermore, the survival of the resulting cell mass derived from the cancer tissue was confirmed by transplanting it into NOD-SCID mice as a mass containing approximately 1,000 cells.

Comparative Example 1

A sample which had been treated to single cells according to the method described in the literature (Todaro M et al., (2007) Colon cancer stem cells dictate tumor growth and resist cell death by production of interleukin-4. Cell Stem Cell 1:389-402) was prepared using surgical specimens of human colon cancer. However, in vitro proliferation was not found in CD133 positive cells that had been selected after treatment into single cells.

Figure 2:
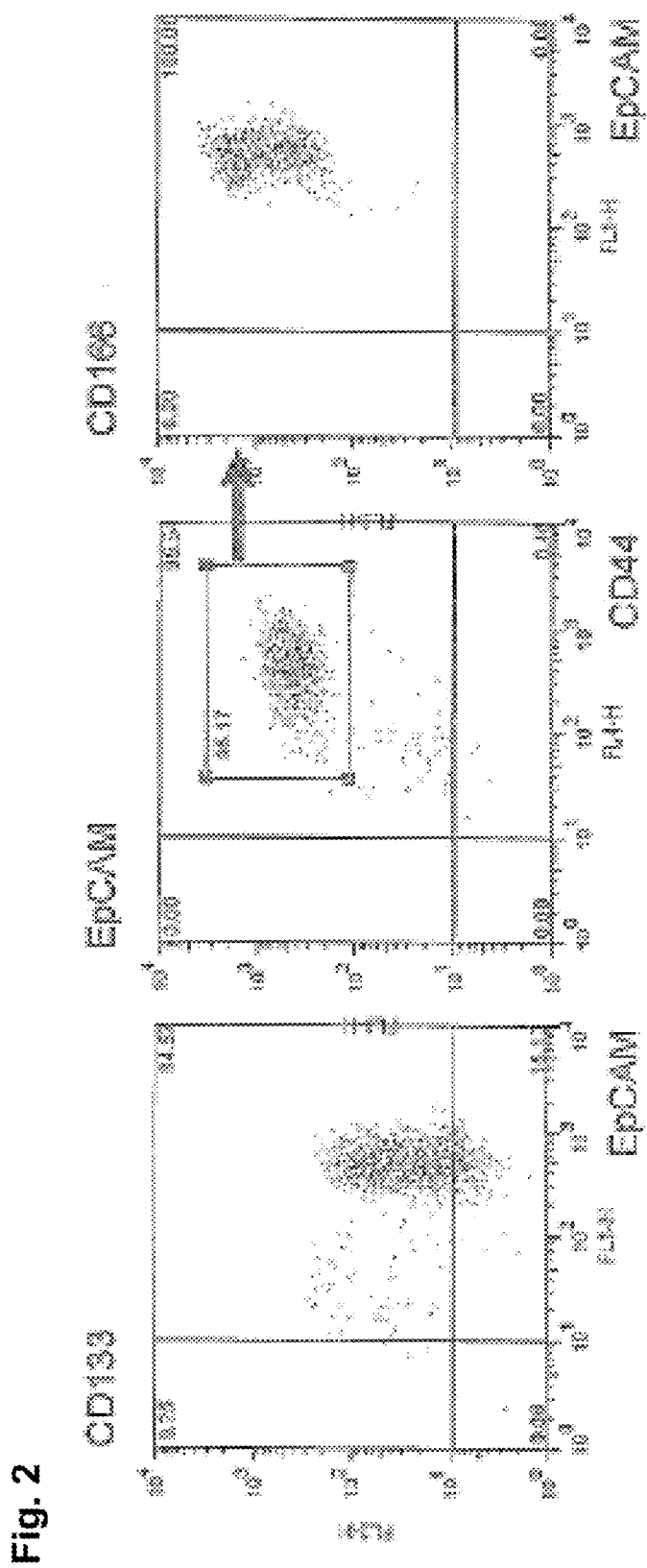
FIG. 2 shows an embodiment of the cell mass derived from a cancer tissue according to the present invention, wherein the cell expresses a surface antigen such as CD133, CD44, CD166, etc.
Figure 3:
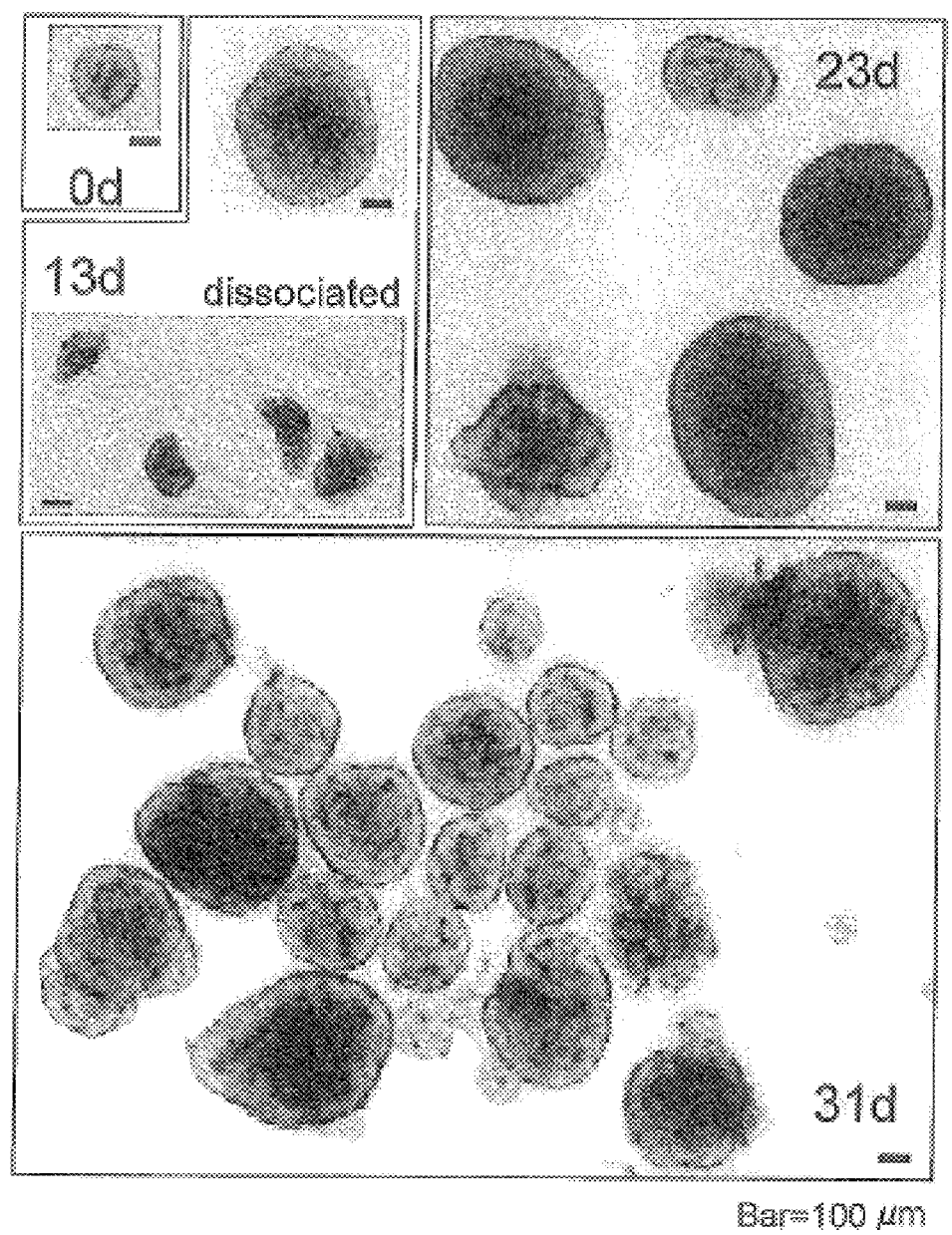
FIG. 3 is a drawing showing the change of form and proliferation ability during the in vitro culture process of the cell mass derived from a cancer tissue according to the present invention.
Figure 4:
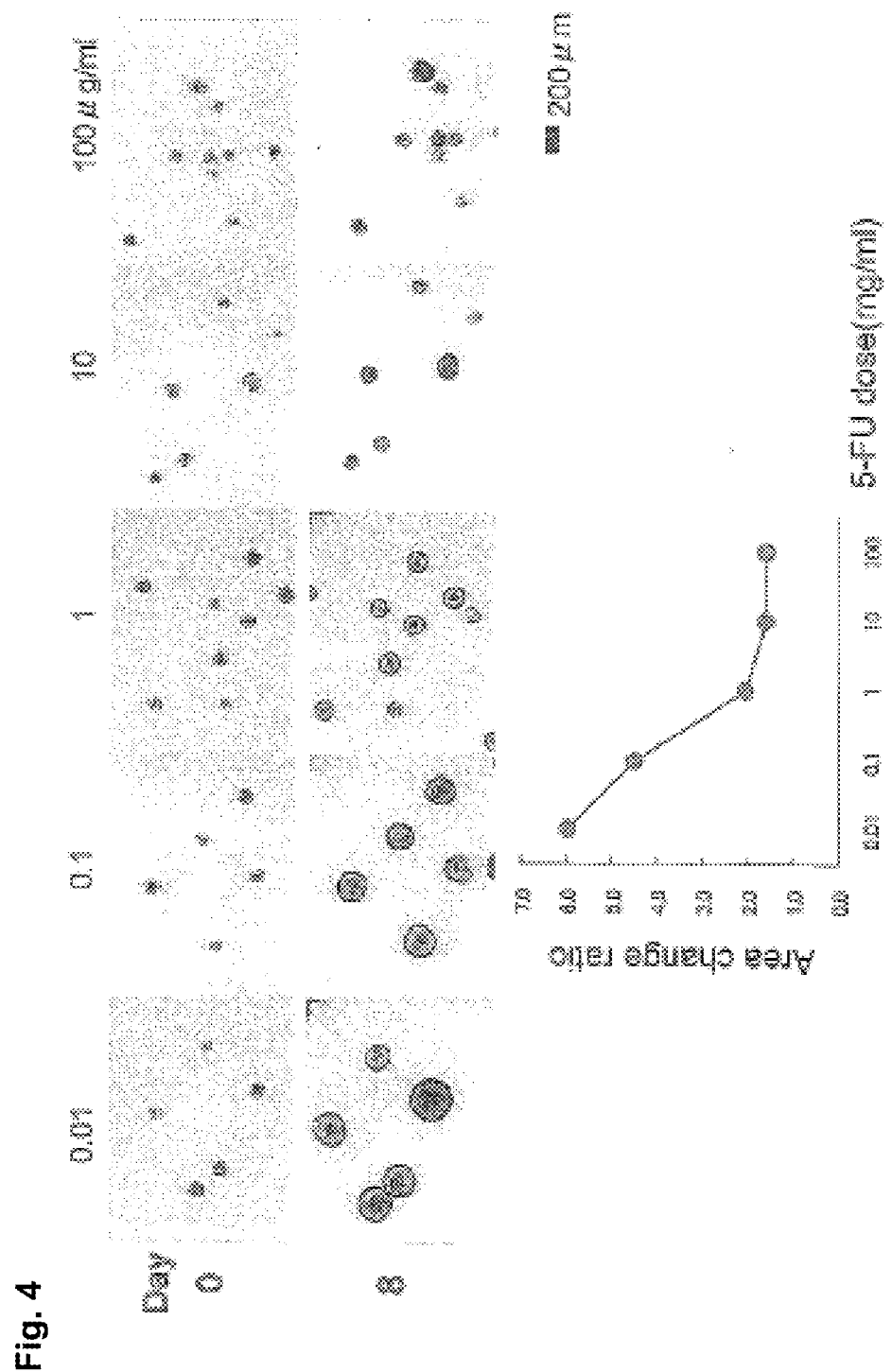
FIG. 4 is a drawing showing the result of an in vitro drug-sensitivity test with 5-FU using the cell mass derived from a cancer tissue according to the present invention.
Figure 5:
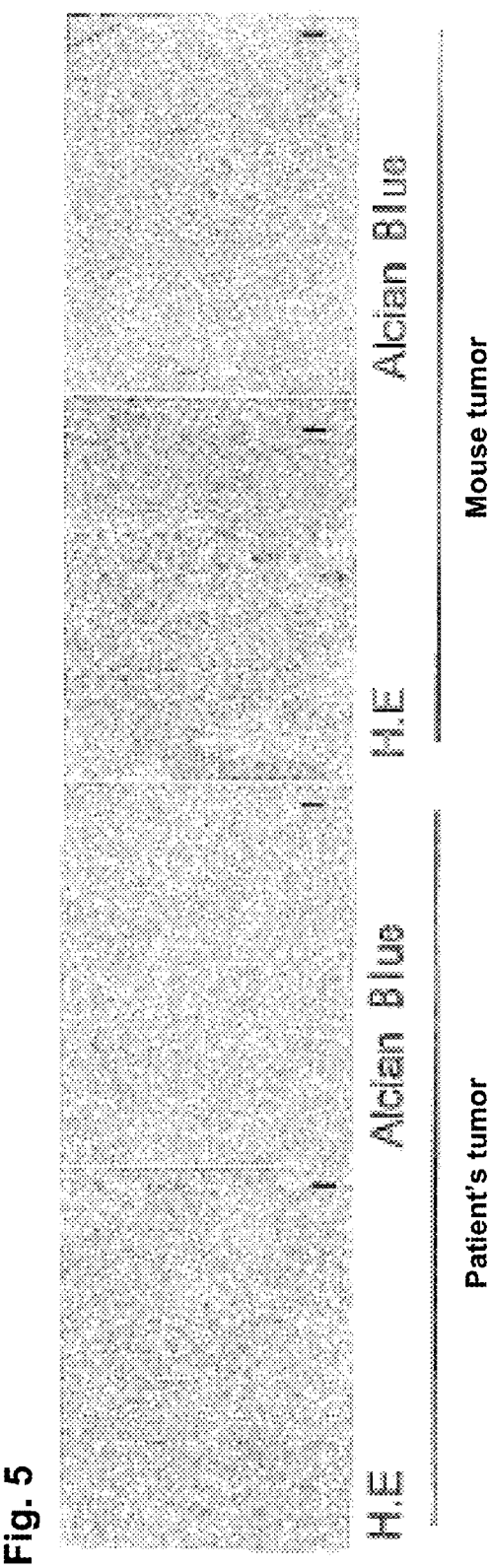
FIG. 5 is a drawing wherein a tumor tissue (right) obtained by transplanting the cell mass derived from a cancer tissue according to the present invention into mice is compared with a tumor tissue (left) that is removed from a living body from which the cell mass derived from a cancer tissue is derived.

Evaluation items in Examples, etc. were measured as follows.
Identification of Surface Antigen The cell mass from the cancer tissue, obtained in Example 1, was dispersed to single cells using trypsin/EDTA. These cells were reacted with a surface antigen-specific antibody that was labeled with a fluorescence substance, and then analyzed by flow cytometry. As a result, the existence of cells that expressed a surface antigen uniformly at the same time was recognized as shown in FIG. 2.
Confirmation of Basement Membrane-Like Material The cell mass derived from the cancer tissue, obtained in Example 1, was cultured for three days in 1 cc of STEMPRO serum-free medium (Gibco) for human ES cells in an incubator under the culture conditions of 37° C. and 5% $CO_2$. Antigenicity of laminin was observed in the cytoplasm of the cell in or near to the circumference of the cell mass derived from the cancer tissue when this was fixed with formalin, embedded in paraffin, cut into thin slices, and anti-laminin antibody staining (mouse laminin-derived rabbit antibody; manufactured by Sigma-Aldrich Corporation) was performed according to the manufacturer's instructions. As a result, in the cell mass derived from a cancer tissue according to the present invention, it was found that laminin surrounded the circumference of a population of the cancer cells. On the other hand, expression of laminin was not confirmed within 24 hours after treatment of surgical specimens.
Detection of Hypoxia
Example of Hypoxia Detection Using Pimonidazole Pimonidazole that is a nitroimidazole compound and has a characteristic to form an adduct with proteins or nucleic acids in the absence of oxygen. The hypoxic region of the tissue treated with pimonidazole under hypoxic conditions can be recognized using an antibody that specifically recognizes pimonidazole. When the cancer tissue was separated by about 100 micrometers from a blood vessel, a hypoxic region appears, and a wide range of cell death was observed inside (hypoxic region) the boundary apart from about 100 micrometers from the circumference of the cell mass derived from the cancer tissue obtained in Example 1.
Evaluation of In Vitro Proliferation Ability The in vitro proliferation ability of the cell mass derived from a cancer tissue was examined as follows. The cell masses (×10 each) derived from the cancer tissue, obtained in Example 1, were embedded in a collagen gel (CellMatrix type IA (Nitta Gelatin Inc.): 5×DMEM (Gibco; 12100-038): buffer solution for gel reconstruction (50 mM NaOH, 260 mM NaHCO3, 200 mM HEPES)=7:2:1), and was cultured in 1 cc of STEMPRO serum-free medium (Gibco) for human ES cells in an incubator under the culture conditions of 37° C. and 5% $CO_2$. The cell state was observed periodically and the size of the cell was measured with a phase contrast microscope (magnification 40 times) equipped with a CCD camera. As a result, without mechanical division, the proliferation ability could be retained for at least 13 days as shown in FIG. 3. Moreover, it was confirmed that the proliferation ability could be retained for further at least 13 days when mechanical division was performed on day 13. In addition, the mechanical division of the cell mass was performed by dividing the cell mass with a diameter of 500 micrometers derived from the cancer tissue into four with an ophthalmic pointed knife.
Confirmation of Cell Count A 100 to 250 μm-sized cell mass derived from a cancer tissue was treated with trypsin 0.25% and EDTA 2.6 mM for three minutes in the same manner as in Example 1, and mechanically degraded by pipetting approximately 30 times. This was diluted and subdivided into a 96-well culture plate so that one cell can be placed in one well. The cell count constituting a cell mass that was non-single celled was counted and recorded. Then, culture (under the conditions as above) was performed to record an increase of the cell count of each well, and the culture was observed for 30 days. As a result, it was confirmed that a cell mass could be even grown up if there were three cells.
Drug Sensitivity Test Using 5-FU which is known to inhibit DNA synthesis by binding to a thymidylic acid synthetase involved in the metabolism process necessary for DNA synthesis, a drug sensitivity test on a sample of Example 2 was carried out. The test was carried out by embedding the cell masses (×10 each) derived from the cancer tissue in a collagen gel (CellMatrix type IA (Nitta Gelatin Inc.):5×DMEM (Gibco; 12100-038): buffer solution for gel reconstruction (50 mM NaOH, 260 mM NaHCO3, 200 mM HEPES)=7:2:1), and culturing in 1 cc of STEMPRO serum-free medium (Gibco) for human ES cells in an incubator under the culture conditions of 37° C. and 5% $CO_2$. In addition, 5-FU was applied at a concentration of 0.01 μg/ml, 0.1 μg/ml, 1 μg/ml, 10 μg/ml, and 100 μg/ml, and the states of the cells on days 0 and 8 after culture were compared for evaluation. The results are shown in FIG. 4. An increasing rate of the area of the cell mass derived from the cancer tissue was expressed relative to 1 of an increasing rate of the area of the cell mass in the culture without application of a drug. In FIG. 4, it was actually demonstrated that proliferation of the cancer cell was concentration-dependently suppressed by 5-FU on day 8 after culture, and the cell mass derived from a cancer tissue according to the present invention was useful in a drug sensitivity test.
Transplantation Test in Different Species of Animals The cell masses (×10) having each a diameter of about 100 μm derived from the cancer tissue, obtained in Example 2 by culture for three days according to the present invention, were suspended in Matrigel (BD Corporation), and the suspension was administered subcutaneously to the back of NOD-SCID mice for transplantation. The evaluation of tumorigenesis was performed by measuring the size of the tumor with the lapse of time. As a result, it was confirmed that a marked tumorigenesis was recognized in a mouse which had been transplanted with the cell mass derived from the cancer tissue of Example 2 of the present invention, and the cell mass derived from the cancer tissue according to the present invention has a high tumorigenic ability. When this tissue was analyzed, it was revealed that a similar tissue type was produced in both the tumor that occurred in transplanted mice and the existing tumor in a living body (FIG. 5).

Radiation Irradiation Test

Figure 6:
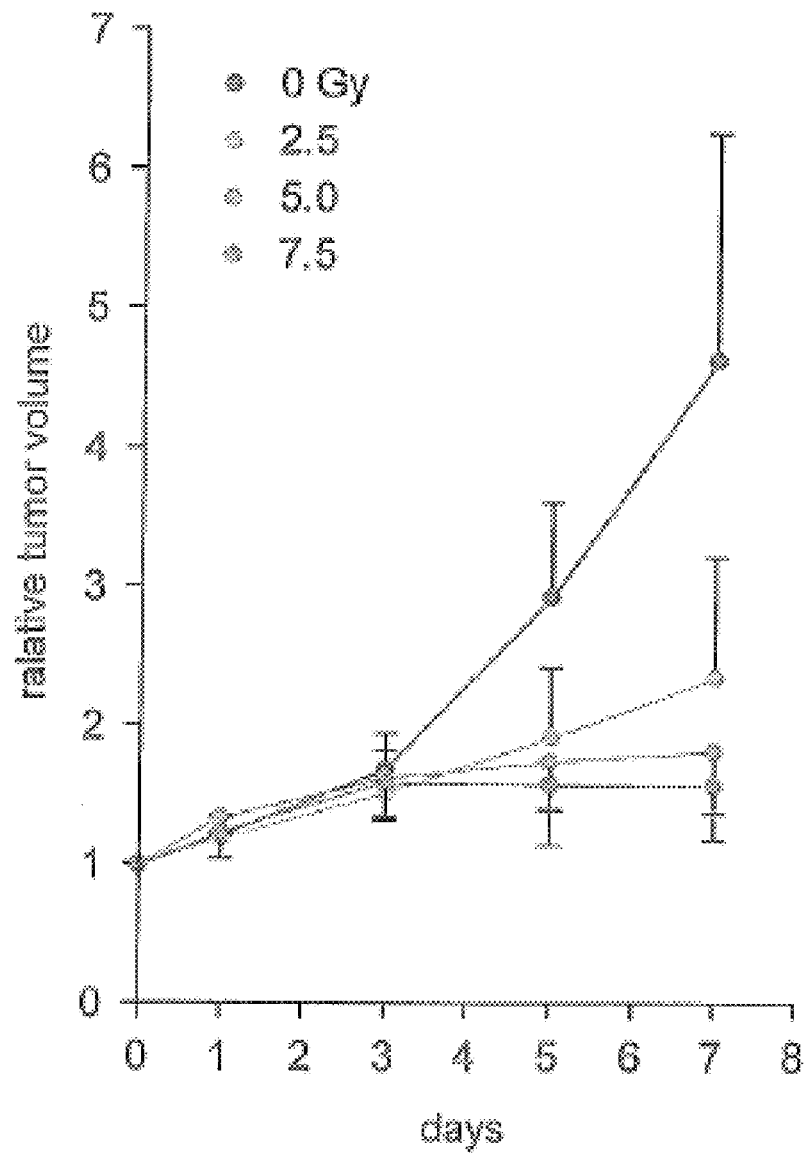
FIG. 6 is a drawing showing the result of an in vitro radiosensitivity test using the cell mass derived from a cancer tissue according to the present invention.

The cell masses derived from the cancer tissue obtained in Example 2 and used in the present invention, having a diameter of about 100 μm, were embedded in a collagen gel (Cell-Matrix type IA (Nitta Gelatin Inc.):5×DMEM (Gibco; 12100-038):buffer solution for gel reconstruction (50 mM NaOH, 260 mM NaHCO3, 200 mM HEPES)=7:2:1), and inoculated (×10 cell masses each) to 1 cc of STEMPRO serum-free medium (Gibco) for human ES cells in an incubator under the culture conditions of 37° C. and 5% $CO_2$ and then cultured. This was irradiated by γ-rays emitted from a cobalt isotope as a radiation source, thereby to confirm the state of the cell mass. The results are shown in FIG. 6. In FIG. 6, it was actually demonstrated that proliferation of the cancer cell until the $8^{th}$ day after culture was suppressed depending on the exposure dose, and the cell mass derived from a cancer tissue according to the present invention was useful in a radiation irradiation test.

What is claimed is:

1. A process for preparing a cancer tissue-derived cell mass comprising the steps of:
    treating, with a collagenase-containing enzyme, a pulverized product of a cancer tissue removed from a living body;
    selecting and collecting a mass containing at least three cancer cells having a diameter or a long diameter of 20 μm to 500 μm or volume average particle size of 20 μm to 500 μm from the enzymatically treated product with a process for assorting the size; and
    culturing the collected mass to obtain a cultured product that takes an almost spherical or ellipsoidal form.

2. The process for preparing a cancer tissue-derived cell mass according to claim 1, wherein the cultured product that takes an almost spherical or ellipsoidal form consists of cells, 99.54% or more of which express EpCAM.

3. The process for preparing a cancer tissue-derived cell mass according to claim 1, wherein the process for assorting the size is done with the use of a sieve.

4. The process for preparing a cancer tissue-derived cell mass according to claim 1, wherein the step of selecting and collecting a mass containing at least three cancer cells is a step of collecting and selecting an oversized component using a sieve with a mesh size of 40 μm and collecting and selecting an undersized component using a sieve with a mesh size of 250 μm.

5. The process for preparing a cancer tissue-derived cell mass according to claim 1, wherein the enzyme is a mixed enzyme comprising at least one protease selected from the group consisting of *C. histolyticum* neutral protease, thermolysin, and dispase; and at least one collagenase selected from the group consisting of collagenase I, collagenase II, and collagenase IV.

6. The process for preparing a cancer tissue-derived cell mass according to claim 1, wherein the pulverized product is in the size of about 2 mm cube.

7. The process for preparing a cancer tissue-derived cell mass according to claim 1, wherein the collagenase-containing enzyme treatment is conducted for 30 to 150 minutes, at the temperature of 25 to 39° C. under the conditions of pH 6~8.

8. The process for preparing a cancer tissue-derived cell mass according to claim 1, wherein the step for culturing is done in a serum-free media which contains EGF or bFGF in the concentration of 10 to 30% w/v based on the whole medium at least three hours.

9. The process for preparing a cancer tissue-derived cell mass according to claim 1, further comprising the step for mechanically dividing the cultured product that takes an almost spherical or ellipsoidal form.

10. The process for preparing a cancer tissue-derived cell mass according to claim 1, wherein the step of selecting and collecting a mass containing at least three cancer cells is a step of collecting and selecting an oversized component using a sieve with a mesh size of 40 μm and collecting and selecting an undersized component using a sieve with a mesh size of 250 μm with the use of a pipette.

* * * * *